United States Patent [19]

Connolly et al.

[11] Patent Number: 5,321,010
[45] Date of Patent: Jun. 14, 1994

[54] PROTEINS FOR INHIBITING ADHESION OF PLATELETS TO COLLAGEN

[75] Inventors: Thomas M. Connolly, Harleysville; Michael Neeper, Wayne; Lloyd Waxman, New Hope, all of Pa.

[73] Assignee: Merck & Co., Inc., Rahway, N.J.

[21] Appl. No.: 807,022

[22] Filed: Dec. 10, 1991

[51] Int. Cl.$^5$ .............................................. A61K 37/00
[52] U.S. Cl. ........................................ 514/21; 514/12; 530/350; 530/858
[58] Field of Search ............... 530/350, 416, 417, 858; 514/12, 21

[56] References Cited

U.S. PATENT DOCUMENTS 5,093,322  3/1992  Bonin et al. ............................ 514/21
5,179,082  1/1993  Connolly et al. ....................... 514/12

OTHER PUBLICATIONS

Ribeiro et al., "Saliva of the Soft Tick Ornithodoros Moubata . . . ", Comp Biochem. Physiol. A Comp Physiol. 100(1), 1991 pp. 109–112. (91:479116 BIOSIS; CA 115(19)203748r).
Jordan et al., "Tick Coagulant Peptide . . . ", Biochemistry 29(50), 1990, pp. 11095–11100 (90: 12443 CJACS).
Fauvel et al., Thrombosis Research 12 (1978) pp. 841–850.
Shadle et al. J. of CellBiol. 99 (Dec. 1984) pp. 2056–2060.
Fauvel & Legrand, Thrombosis Research 17 (1980) pp. 285–287.
Legrand et al., J. Lab. Clin. Med. 94 (1979) pp. 438–446.
Studier & Moffatt, J. Mol. Biol. 189 (1986) pp. 113–130.
Rosenberg et al., Gene 56 (1987) pp. 125–135.
Shadle & Barondes, J. of Cell Biol. 99 (Dec. 1984) pp. 2048–2055.

Primary Examiner—Michael G. Wityshyn
Assistant Examiner—C. Sayala
Attorney, Agent, or Firm—Richard S. Parr; Melvin Winokur; Paul D. Matukaitis

[57] ABSTRACT

The invention comprises proteinaceous substances isolated from crude *Ornithodoros moubata* extract which inhibit adhesion of platelets to collagen. These substances do not inhibit platelet adhesion to fibrinogen, and are therefore particularly useful for inhibiting adhesion of platelets to collagen when simultaneous inhibition of platelet adhesion to fibrinogen is undesired. They are particularly useful in the prevention, prophylaxis, therapy and treatment of thrombotic diseases.

3 Claims, 2 Drawing Sheets

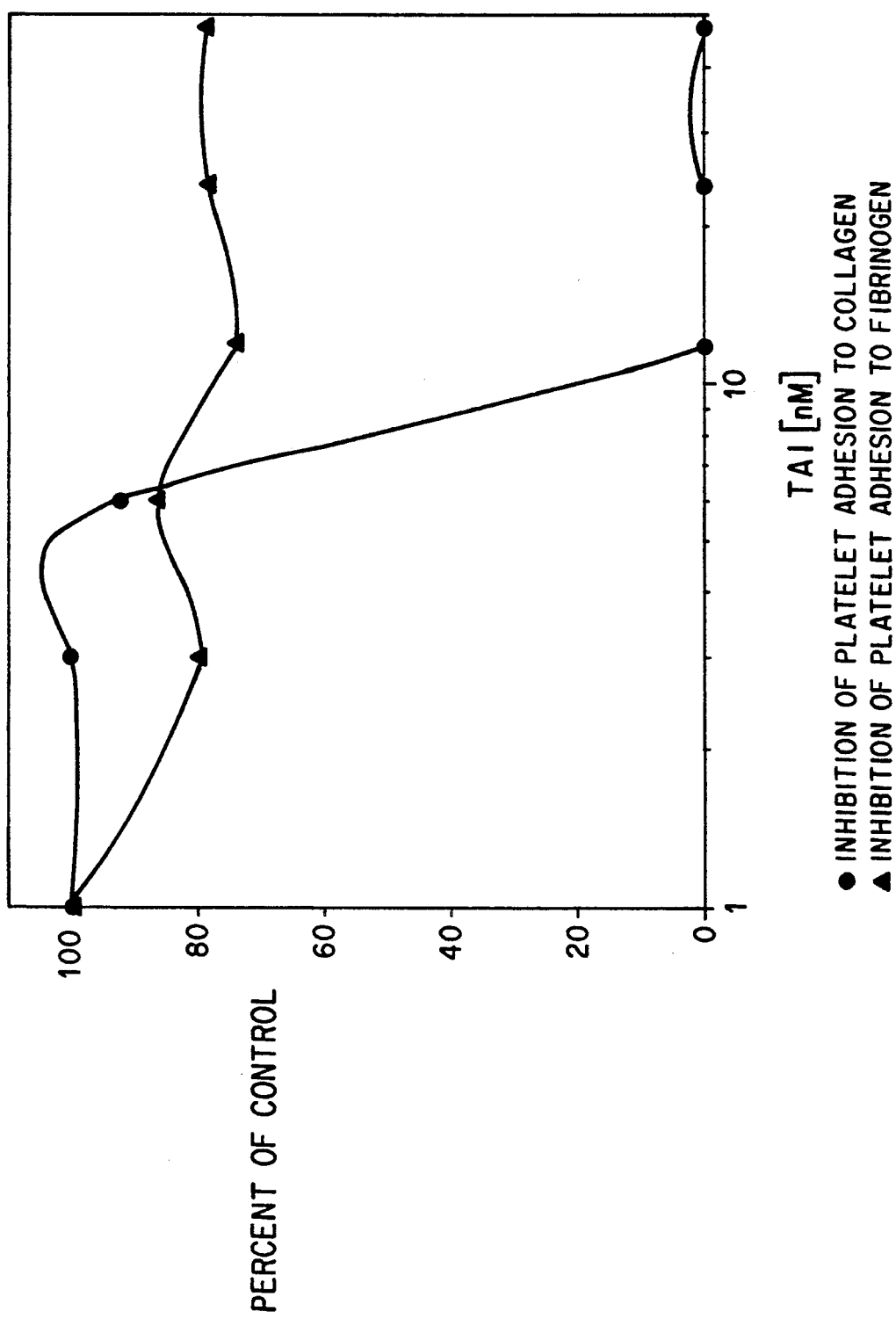

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 202 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:1:

```
Lys Leu Ala Ile Leu Ala Val Cys Val Phe Ile Ser Thr Val Ser Ser
 1               5                  10                  15

Val Pro Thr Ser Asp Thr Ser Glu Glu Glu Asp Leu Asn Thr Lys Asn
            20                  25                  30

Arg Asp Ile Trp Lys Thr Tyr Ser Lys Ser Lys Val Phe Trp Leu Leu
            35                  40                  45

Arg Arg Thr Tyr Trp Val Asp Gly Lys Arg Ser Leu Cys Arg Tyr Gly
    50                  55                  60

Thr Val Leu Lys Arg Asp Lys Ala Asn His Arg Ile Glu Gln Ile Met
65                  70                  75                  80

Gly Ser Tyr Asp Glu Ser Gln Glu Thr Tyr Thr Lys Thr Lys Val Tyr
                85                  90                  95
```

```
Ile Thr Thr Arg Leu Gly Arg Ser Gly Asp Arg Asn His Met Gly Val
        100                 105             110
Ser Leu Gln Gly Tyr Asn His Thr Gly Ile Glu Tyr Lys Met Ile Tyr
        115                 120             125
Asp Asp Asp Gln Gly Cys Ala Ile Leu Lys Val Thr Lys Asp Asn Arg
        130             135         140
Asn Gln Pro Gln Asn Leu Lys Asn Ala Cys Glu Met Trp Ala Thr Ala
145                 150             155                     160
Asn Asp Ala Asn Ser Val Asn Ser Ile Ala Ala Cys Glu Val Val Tyr
                165             170                 175
Gln Arg Arg Cys Asn Pro Asn Asn Ser Val Asp Asp Thr Pro Tyr Val
            180             185             190
Thr Thr Cys Lys Trp Pro Pro Val Glu Leu
        195             200
```

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:2:

```
Asn Ala Cys Glu Met Trp Ala Thr Ala Asn Asp
1               5                   10
```

PROTEINS FOR INHIBITING ADHESION OF PLATELETS TO COLLAGEN

BACKGROUND OF THE INVENTION

Normal hemostasis in man is governed by a complex series of interrelated mechanisms involving both cellular and humoral biochemical components. The biochemical pathway involves injury to intact endothelial cells, stimulation of platelets and activation of coagulation mechanisms. When a vessel is damaged and the subendothelium is exposed, platelets rapidly adhere to some of the constituents of the vessel wall, notably collagen. Although platelets also adhere to other subendothelial constituents, only collagen has been reported to stimulate platelets to release their granule contents and recruit other platelets to the injury site.

SUMMARY OF THE INVENTION

The invention comprises proteinaceous substances isolated from crude *Ornithodoros moubata* extract which inhibit adhesion of platelets to collagen. These substances do not inhibit platelet adhesion to fibrinogen, and are therefore particularly useful for inhibiting adhesion of platelets to collagen when simultaneous inhibition of platelet adhesion to fibrinogen is undesired. They are particularly useful in the prevention, prophylaxis, therapy and treatment of thrombotic diseases.

Furthermore, these substances do not block platelet adhesion to fibronectin, nor do they block endothelial cell adhesion to fibronectin.

One protein of the present invention, referred to as "TAI-1"(SEQID No. 1:, has a molecular weight of about 23,000. Another protein of the invention, referred to as "TAI-4", has a molecular weight of about 15,600.

The invention also comprises methods for purifying the proteins from *Ornithodoros moubata* extract, and methods for using the proteins to prevent or delay blood coagulation by blocking adhesion of platelets to collagen.

The invention also comprises a method for producing TAI-1 in *E. coli* DE3 BL21 using recombinant techniques.

DESCRIPTION OF THE FIGURES

FIG. 2 shows the inhibitory effect of TAI-4 on platelet adhesion to collagen. FIG. 3 illustrates the construction of pET3A-TAI-1.

DETAILED DESCRIPTION OF THE INVENTION

Figure 1:
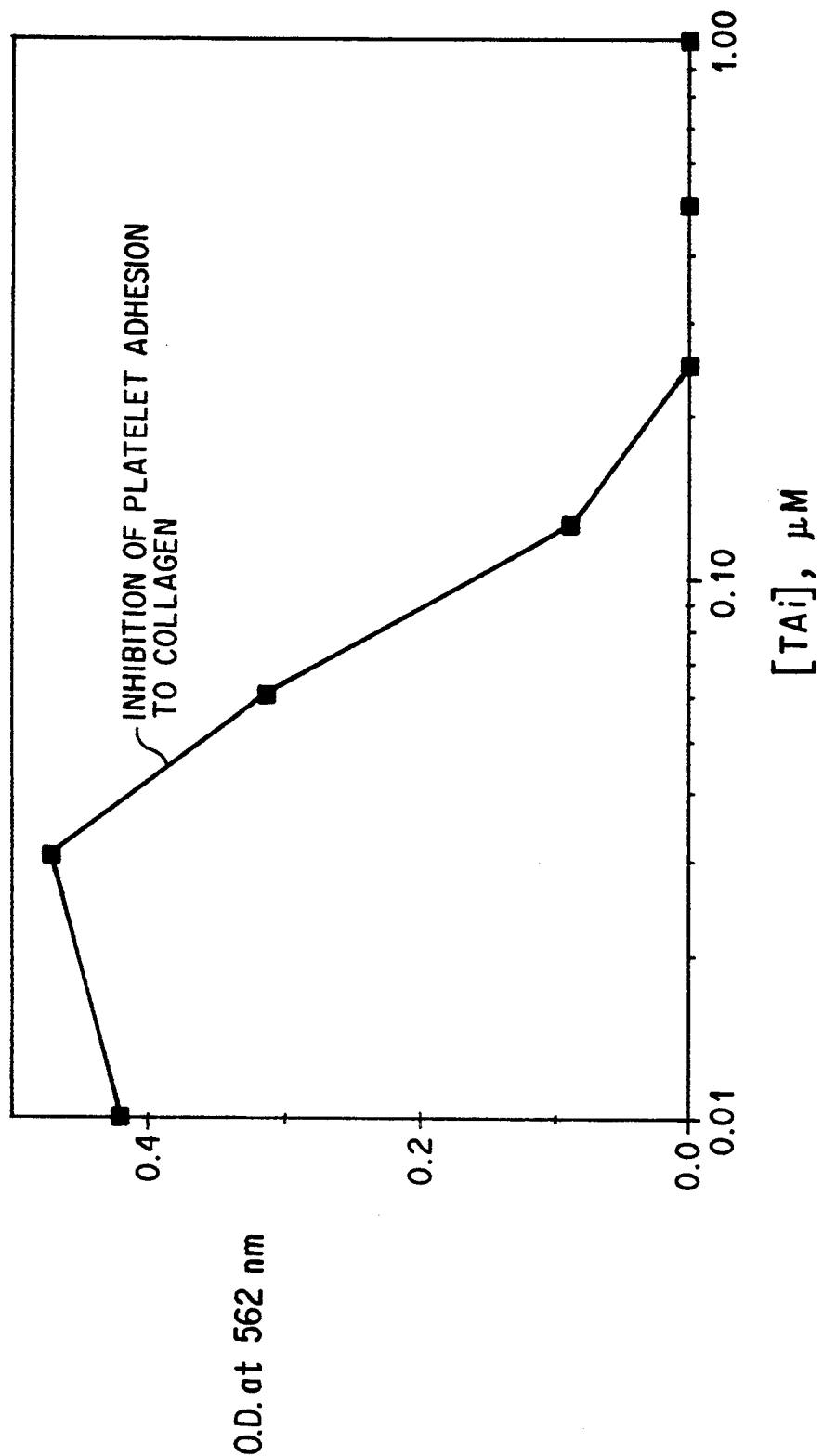
FIG. 1 shows the inhibitory effect of TAI-1 on platelet adhesion to collagen.

The invention encompasses the proteins isolated from *Ornithodoros moubata* and homologs, isoforms or genetic variants, provided that each one blocks adhesion of platelets to collagen and reacts with antibodies specific for the specified proteins.

Proteins

Proteins of the invention include variations on the disclosed purified protein sequences which conserve the activity of the disclosed sequences, including fragments or subunits, naturally occurring mutations, allelic variants, randomly generated artificial mutants and intentional sequence variation which conserves activity. Fragments or subunits refers to any portion of the sequence which contains fewer amino acids than the complete protein, e.g. partial sequences excluding portions at the N- and/or C-termini of the complete protein.

Proteins of the invention also include recombinant protein sequences which conserve the activity of the purified protein sequences, and hybrid proteins, such as fusion proteins or proteins resulting from the expression of multiple genes within the expression vector having said activity, and may include a polypeptide having the specific activity of a disclosed protein linked by peptide bonds to a second polypeptide.

It will be understood that other variants of the proteins of the present invention are included, especially any variants that differ from the isolated protein only by conservative amino acid substitution. Such conservative amino acid substitutions are defined as "sets" in Table I of Taylor, *J. Mol. Biol.*, 188, 233 (1986).

Proteins of the present invention may also be prepared by recombinant techniques, or obtained from crude *Ornithodoros moubata* extract as described below.

Inhibition of Platelet Adhesion to Collagen

Platelets were isolated from healthy human volunteers who had abstained from aspirin and other drugs for at least 8 days. 100 ml of blood was drawn into 8 ml acid citrate dextrose, then centrifuged at 200 ×g for 20 minutes. The platelet-rich plasma was removed and prostaglandin $E_1$ (PGE$_1$) was added at a final concentration of 1 uM followed by pelleting the platelets by centrifugation at 800 ×g for 10 minutes. The platelets were resuspende in a modified Tyrode's buffer without Ca$^{++}$(134 mM NaCl, 3 mM KCl, 0.3 mM NaH$_2$PO$_4$, 2mM MgCl$_2$, 5 mM HEPES, 5 mM glucose, 12 mM NaHCO$_3$, 1 mM EGTA and 3.5 mg/ml BSA at pH 6.5 and apyrase at 20 ug/ml. The platelet suspension was sedimented by centrifugation and the platelets washed one more time. The final pellet was resuspended in final buffer (wash buffer at pH 7.4 with no EGTA) and adjusted to $3 \times 10^8$ platelets/ml after counting in a model ZM Coulter Counter (Hialeah, Fla.).

Platelet adhesion to collagen was measured in polystyrene 96-well microtiter plates (Costar, Cambridge, Mass.). Plates were coated with 50 ul per well of 40 ug/ml collagen dissolved in 5 mM acetic acid or fibrinogen in phosphate buffered saline for 1 hour at room temperature followed by blocking of the non-specific cell binding sites by addition of 200 ul of 10 mg/ml heat-debatured BSA for 1 hour. Control wells were coated with BSA only. The wells were rinsed three times with HEPES buffered saline (HBS) containing 20 mM HEPES, pH 7.4, 0.14 m NaCl, and 2mM MgCl$_2$. 100 ul of washed platelets at $3 \times 10^8$/ml were added to each well and incubated at room tepmerature for 45 minutes, nonadherent platelets were removed by aspiration, and the wells were rinsed three times with 200 ul of HBS. The number of adhered platelets was determined by protein assay, using the BCA reagent (Pierce Chemical Co., Rockford, Ill.).

Protein Isolation

*Ornithodoros moubata* ticks were obtained from South Africa through Antibody Associates, Inc. (Bedford, Tex.). One hundred whole ticks (7.5 g) were homogenized in batches of 50 ticks with a Polytron in 10 ml of 20 mM Bis-Tris-HCl (pH 7.0) containing 0.15 M NaCl and the protease inhibitors E-64, pepstatin, chymostatin and leupeptin (50 uM each). The homogenate was centrifuged at 100,000 ×g/20 minutes and the resulting pellets were re-extracted. Specific procedures for preparing TAI-1 and TAI-4 follow.

EXAMPLE 1

Isolation of TAI-1

Combined supernatants were diluted 2-fold with water and applied at 1 ml per minute to a 50 ml column of Fast Q Sepharose anion exchange resin equilibrated with 20 mM Bis-Tris-HCl (pH 7.0). The column was washed with 2 volumes of the same buffer and the wash was combined with the flow through. This material was lyophilized, redissolved and chromatographed on Sephadex G-50. The active fractions (those that inhibit platelet adhesion to collagen) were applied to a Mono S HPLC cation exchange column equilibrated in 20 mM sodium acetate buffer (pH 5.0). After washing with the same buffer, the bound sample was eluted with a gradient of sodium chloride (0 to 0.6 M) in the same buffer. After rechromatography of the active fractions which elute at 0.3 M sodium chloride on the same column, SDS-PAGE of the purified material showed 1 band. Approximately 100 ug of the 23,000 molecular weight protein was obtained from 100 ticks.

FIG. 1 shows that TAI-1 inhibits platelet adhesion to collagen with an $IC_{50}$ of about 90 nM. We have also demonstrated that TAI-1 does not inhibit platelet adhesion to fibrinogen and that it does not inhibit platelet adhesion to fibronectin.

EXAMPLE 2

Isolation of TAI-4

The flow through and wash of Fast Q was passed over a Sepharose cation exchange column equilibrated in 20 mM sodium acetate buffer, pH 5.0. After washing with the same buffer, the sample was eluted with a 0–1 M NaCl gradient in the same buffer. The peak fractions that inhibited platelet adhesion to collagen were pooled and adjusted to 2M ammonium sulfate and applied to a phenyl-superose FPLC column in 25 mM phosphate, pH 7.0, containing 2M ammonium sulfate and eluted by lowering the ionic strength to 0 ammonium sulfate. The peak fractions were applied to a Bio-Sil SEC-125 HPLC size exclusion column and the purified protein eluted a peak that was a single band on a gel (molecular weight of 15,600).

FIG. 2 shows that TAI-4 inhibits platelet adhesion to collagen and does not inhibit platelet adhesion to fibrinogen. TAI-4 also does not inhibit platelet adhesion to fibronectin. We have also demonstrated that TAI-4 inhibits adhesion of endothelial cells to collagen.

Amino acid composition analysis of the two isolated proteins showed the following:

| Amino Acid | Residues/mole TAI-1** | TAI-4 |
|---|---|---|
| Asx | 27.7 | 12.3 |
| Thr | 16.6 | 10.4 |
| Ser | 15.1 | 17.3 |
| Glx | 19.4 | 19.8 |
| Gly | 14.6 | 15.9 |
| Ala | 9.0 | 8.6 |
| Cys | 2.7* | 4* |
| Val | 12.4 | 9 |
| Ile | 7.7 | 3.7 |
| Leu | 10.9 | 9 |
| Tyr | 10.5 | 3.7 |
| Phe | 0.3 | 4 |

-continued

| Amino Acid | Residues/mole TAI-1** | TAI-4 |
|---|---|---|
| His | 3.4 | 1.9 |
| Lys | 15.0 | 6.9 |
| Arg | 12.7 | 7.9 |
| Pro | 5.9 | 8.9 |
| Trp | 3.7* | 2* |
| Met | 3.0 | 1.3 |

*estimate based on size of protein
**based on the molecular weight of the deduced amino acid sequence from the cDNA (21,500)

Recombinant DNA Technology

Recombinant DNA technology may be used to produce proteins of the invention. This technology allows segments of genetic information, DNA, from different cells, and usually from different organisms, to be joined end-to-end outside the organisms from which the DNA was obtained and to incorporate this hybrid DNA into a cell that will allow the production of the protein for which the original DNA encodes. Genetic information, DNA or mRNA, is isolated and incorporated into an appropriate cloning vector, and transduced into an appropriate host cell.

Cloning vectors useful for this technology include a DNA-sequence which accommodates specific experimental foreign DNA. The vectors are introduced into host cells that can exist in a stable manner and express the protein dictated by the experimental DNA.

Expression vectors are DNA sequences that are required for the transcription of cloned copies of genes and the translation of their mRNAs in an appropriate host. A suitably constructed expression vector contains an origin of replication for autonomous replication in host cells, selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency. Expression vectors may include, but are not limited to cloning vectors, modified cloning vectors and specifically designed plasmids or viruses.

Procarvotic Expression Systems

Procaryotes most frequently are represented by various strains of *E. coli*. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., Gene (1977) 2:95. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., Nature (1977) 198:1056) and the tryptophan (Trp) promoter system (Goeddel et al., *Nucleic Acids Res.* (1980) 8:4057) and the lambda-derived $P_L$ promoter and N-gene ribosome binding site (Shimatake et al., Nature (1981) 292:128).

Preferably, the expression system used to produce TAI-1 is *E. coli* BL21 (DE3) (Studier and Moffatt, *J. Mol. Biol.* (1986) 189, pp. 113–130).

The lambda cloning vector D69, having a single BamHI cloning site within the int gene, was used (Mizusawa & Ward, Gene 20 (1982) pp. 317-322). A derivative of D69 was prepared by cloning a lacUV5 promoter into the int gene to produce the DE3 phage. The BL21 (DE3) lysogen, under the control of the lacUV5 promoter, provides an inducible source of T7 RNA polymerase having a basal level sufficiently low that most T7 genes can be maintained under control of the T7 promoter.

E. coli BL21 (DE3) (available from Novagen (Madison, Wisc.)) grows as well in the continuous presence of IPTG (isopropyl-beta-D-thiogalactophranoside), which induces polymerase expression, as in its absence.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Preferably, the vector used to express TAI-1 is pET3A (Rosenberg et al., Gene 56 (1987) pp. 125-135) (available from Novagen (Madison, Wisc.)). FIG. 1 on page 126 of Rosenberg et al. shows that pET3A was prepared by inserting the T7 promoter, the gene 10 translation start site and the transcription terminator into the BamHI site of pBR322. pET3A also includes unique cloning sites NdeI and NheI. Restriction endonucleases and enzymes used in cloning were purchased from New England Biolabs, Bethesda Research Laboratories or Boehringer-Mannheim.

Site specific DNA cleavage is performed by treating with the suitable restriction enzyme (or enzymes) under conditions which are generally understood in the art, and the particulars of which are specified by the manufacturer of these commercially available restriction enzymes. See, e.g. New England Biolabs, Product Catalog. In general, about 1 μg of plasmid or DNA sequence is cleaved by one unit of enzyme in about 20 μl of buffer solution. Typically, an excess of restriction enzyme is used to ensure complete digestion of the DNA substrate. Incubation times of about 1 to 2 hours at about 37° C. are workable, although variations can be tolerated. After each incubation, the digestion product is exposed to phenol/chloroform extraction and may be followed by running over a Sephadex ®G-50 spin column. If desired, size separation of the cleaved fragments may be performed by polyacrylamide gel or agarose gel electrophoresis using standard techniques. A general description of size separations is formed in *Methods in Enzymology* (1980)65: 499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° to 25° C. in 50 mM Tris, pH 7.6, 50 mM NaCl, 6mM MgCl₂, 6mM DTT and 5-10 μMdNTPs. The Klenow fragment fills in 5'overhangs but removes protruding 3'single strands, even in the process of the four dNTPs. If desired, selective repair can be performed by supplying selected dNTPs within the limitations dictated by the nature of the sticky ends. After treatment with Klenow, the mixture is extracted with phenol/chloroform and ethanol precipitated followed by running over a Sephadex ®G-50 spin column. Treatment under appropriate conditions with S1 nuclease results in hydrolysis of any single-stranded portion.

As mentioned above, oligonucleotides may be prepared by the triester method of Matteucci, et al. (*J. Am. Chem. Soc.* (1981) 103:3185) or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl₂, 5mM dithiothreitol, 1-2 mM ATP, 1.7 pmoles ³²P-ATP(2.9 mCi/mmole), 0.1 mM spermidine, 0.1 mM EDTA.

Ligations are performed in 15-30 μl volumes under the following standard conditions and temperatures: 20 mM Tris-HCl, pH 7.5, 10 mM MgCl₂, 10 mM DDT, 33μg/ml BSA, 10 mM-50 mM NaCl, and 1 mM ATP, 0.3-0.6 (Weiss) units T4 DNA ligase at 14° C. (for "blunt end" ligation). Intermolecular "sticky end" ligations are usually performed at 33-100 μg/ml total DNA concentrations (5-100 nM total end concentration). Intermolecular blunt end ligations usually employing a 10-30 fold molar excess of linkers) are performed at 1 μM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na⁺ and Mg²⁺ using about 1 unit of BAP per μg of vector at 60° C. for about 1 hour. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded plasmid or phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered.

cDNA Isolation

Poly A+ RNA is isolated using the guanidinium method of Chirgwin et al., *Biochemistry* 18 pp. 5294-5299 (1979), reverse transcribed into cDNA, according to Maniatis et al., Molecular Cloning, a Laboratory Manual, Cold Spring Harbor Laboratory, Cold Spring Harbor, N.Y. (1982). It is inserted into a lambda ZAP II vector (Stratagene, La Jolla, Calif.) and packaged into a phage as suggested by Stratagene.

Probing cDNA Libraries cDNA or genomic libraries are screened using the colony or plaque hybridization procedure. Each plate containing bacterial colonies (or recombinant phage-infected bacteria) is replicated onto duplicate nitrocellulose filter papers (S & S type BA-85) and, for bacterial colony screens, the colonies are allowed to grow at 37° C. for 14-16 hours on L agar containing 50 µg/ml Amp. The bacteria are lysed, plasmid or phage and DNA fixed to the filter by sequential treatment for 5 minutes each with 0.2N NaOH, 1.5M NaCl, then 0.5 M Tris pH 7.5, 1.5M NaCl and then 2× standard saline citrate (2×SSC). Filters are air dried and baked at 80° C. for 2 hours. The duplicate filters are prehybridized at 42° C. for 6-8 hours with 10 ml per filter of DNA hybridization buffer (5× SSC, pH 7.0, 5× Denhardt's solution (polyvinyl pyrrolidine, plus Ficoll and bovine serum albumin; 1×0.02% of each), 50 mM sodium phosphate buffer at pH 7.0, 0.2% SDS, 20 µg/ml polyU, and 50 µg/ml denatured salmon sperm DNA.

The samples are hybridized with kinased probe under conditions which depend on the stringency desired. Typical moderately stringent conditions employ a temperature of 42° C. for 24-36 hours with 1-5 ml/filter of DNA hybridization buffer containing probe. For higher stringencies, high temperatures and shorter times are employed. The filters are washed four times for 30 minutes each time at 37° C. with 2×SSC, 0.2% SDS and 50 mM sodium phosphate buffer at pH 7, then are washed twice with 2×SSC and 0.2% SDS, air dried and are autoradiographed at −70° C. for 2 to 3 days.

Oligonucleotide Primers

Oligonucleotide primers are prepared which will hybridize to different strands of the desired sequence and at relative positions along the sequence such that an extension product synthesized from one primer, when it is separated from its template (complement), can serve as a template for extension of the other primer into a nucleic acid of defined length. The primers may be prepared using any suitable method, such as, for example, the phosphotriester and phosphodiester methods, described respectively in Narang, S. A. et al. *Meth. Enzymol.*, 68, 90 (1979) and Brown, E. L. et al., *Meth. Enzymol.* 68, 109 (1979), or automated embodiments thereof. In one such automated embodiment, diethylphosphoramidites are used as starting materials and may be synthesized as described by Beaucage et al., *Tetrahedron Letters* (1981), 22: 1859-1862. One method for synthesizing oligonucleotides on a modified solid support is described in U.S. Pat. No. 4,458,066. It is also possible to use a primer which has been isolated from a biological source (such as a restriction endonuclease digest).

Polymerase Chain Reaction Amplification

Large amounts of DNA coding for the protein may be obtained using polymerase chain reaction (PCR) amplification techniques as described in Mullis et al., U.S. Pat. No. 4,800 159. The extension product of one primer, when hybridized to another primer, becomes a template for the production of the nucleic acid sequence.

The primer template complexes act as substrate for DNA polymerase which, in performing its replication function, extends the primers. The region in common with both primer extensions, upon denaturation, serves as template for a repeated primer extension.

Taq DNA Polymerase catalyzes primer extension in the amplification process. The enzyme is a thermostable DNA polymerase isolated from *Thermus aquaticus*. Because it stays active through repeated elevations to high denaturation temperatures, it needs to be added only once. Deoxynucleotide triphosphates provide the building blocks for primer extension.

The nucleic acid sequence strands are heated until they separate, in the presence of oligonucleotide primers that bind to their complementary strand at a particular site of the template. This process is continued with a series of heating and cooling cycles, heating to separate strands, and cooling to reanneal and extend the sequences. More and more copies of the strands are generated as the cycle is repeated. Through amplification, the coding domain and any additional primer-encoded information such as restriction sites or translation signals (signal sequences, start codohs and/or stop codons) is obtained. PCR protocols are often performed at the 100 µL scale in 0.5-mL microcentrifuge tubes. The PCR sample may be single- or double-stranded DNA or RNA. If the starting material is RNA, reverse transcriptase is used to prepare first strand cDNA prior to PCR. Typically, nanogram amounts of cloned template, up to microgram amounts of genomic DNA, or 20,000 target copies are chosen to start optimization trials.

PCR primers are oligonucleotides, typically 15 to 30 bases long, and are complementary to sequences defining the 5' ends of the complementary template strands. Non-template complementary 5' extensions may be added to primers to allow a variety of useful post amplification operations on the PCR product without significant perturbation of the amplification itself. It is important that the two PCR primers not contain more than two bases complementary with each other, especially at their 3' ends. Internal secondary structure should be avoided in primers.

Because Taq DNA Polymerase has activity in the 37°-55° C. range, primer extension will occur during the annealing step and the hybrid will be stabilized. The concentrations of the primers are preferably equal in conventional PCR and, typically, within 0.1-to 1-µM range.

In the standard PCR protocol, each deoxynucleotide triphosphate concentration is preferably about 200 µM. The four dNTP concentrations are preferably above the estimated Km of each dNTP (10-15 µM).

Preferably, PCR buffer is composed of about 500 mM potassium chloride, 100 mM Tris-HCl (pH 8.3 at room temperature), 15 mM magnesium chloride, and 0.01% w/v gelatin. In the presence of 0.8 mM total dNTP concentration, a titration series in small increments over the 1.5-to 4-mM range will locate the magnesium concentration producing the highest yield of a specific product. Too little free magnesium will result in no PCR product and too much free magnesium may produce a variety of unwanted products.

Preferably, in a 100-µLreaction volume, 2.0 to 2.5 units of Taq DNA Polymerase are recommended. The enzyme can be added conveniently to a fresh master mix prepared for a number of reactions, thereby avoiding accuracy problems associated with adding individual 0.5-µL enzyme aliquots to each tube. A typical PCR protocol for amplification of the DNA template includes a 1 minute 94° C. denaturation step, a 1 minute 37° C. primer annealing step, and a 2 minute 72° C. primer extension step. This will amplify a 500 base-pair product at least 100,000-fold in 25 cycles.

During DNA denaturation, sufficient time must be allowed for thermal equilibration of the sample. The practical range of effective denaturation temperatures for most samples is 92°-95° C., with 94° C. being the standard choice.

Primer annealing is usually performed first at 37° C., and the specificity of the product is evaluated. If unwanted bands are observed, the annealing temperature should be raised in subsequent optimization runs. While the primer annealing temperature range is often 37°-55° C., it may be raised as high as the extension temperature in some cases. Merging of the primer annealing and primer extension steps results in a two-step PCR process.

Primer extension, in most applications, occurs effectively at a temperature of 72° C. and seldom needs optimization. In the two-temperature PCR process the temperature range may be 65°-70° C. In situations where enzyme concentration limits amplification in late cycles, the extension is preferably increased linearly with cyclic number. Usually, 25 to 45 cycles are required for extensive amplification (i.e., 1,000,000 fold) of a specific target.

Transformation

Depending on the host cell used, transformation is done using standard techniques appropriate to such cells. The calcium treatment employing calcium chloride, as described by Cohen, S. N., *Proc. Natl. Acad. Sci. USA* (1972) 69:2110, or the RbCl method described in Maniatis et al., *Molecular Cloning: A Laboratory Manual* (1982) Cold Spring Harbor Press, p.254 is used for procaryotes or other cells which contain substantial cell wall barriers. Infection with *Agrobacterium tumefaciens* (Shaw, C. H., et al., Gene (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al., *J. Bacter.* (1977) 130:946 and Hsiao, C. L. et al., *Proc. Natl. Acad. Sci. USA* (1979) 76:3829.

EXAMPLE 3 cDNA Isolation

Poly A+ RNA (polyadenylated mRNA) was isolated from *O. moubata* ticks using the guanidinium method of Chirgwin et al., *Biochemistry* 18 pp. 5294-5299 (1979). During initial stages of extraction, ribonuclease activity was minimized by denaturing the cellular protein, including ribonuclease, at a rate that exceeds the rate of RNA hydrolysis by ribonuclease. Guanidinium thiocyanate, together with a reducing agent, 2-mercaptoethanol, were used to break up protein disulfide bonds. RNA was isolated from the protein by phenol/chloroform extraction, ethanol precipitation or sedimentation through cesium chloride. RNA can also be separated from the protein by extraction with guanidine hydrochloride followed by extraction with phenol/chloroform.

Polydenylated mRNA was separated from the extracted protein by chromatographing the polyadenylated mRNA on oligo (dT)-cellulose as described by Edmonds et al., *Proc. Natl. Acad. Sci.*, 68:1336 (1971); Aviv and Leder, *Proc. Natl. Acad. Sci.*, 69:1408 (1972); and Maniatis et al. (supra at p. 197). The oligo (dT)-cellulose column was prepared with a loading buffer and then the mRNA applied to the column. Thereafter, the column was initially washed with a buffer solution to remove the unpolyadenylated mRNA and then the polyadenylated mRNA was eluted from the column with a buffered, low ionic strength eluant. The integrity of the polyadenylated mRNA was verified by gel electrophoresis.

A library of double-stranded cDNA corresponding to the mRNA was constructed by employing the enzyme reverse transcriptase. The procedure employed is detailed by Maniatis et al., supra at 230, as modified by Gubler and Hoffman, Gene, 25:263-269 (1983). The polyadenylated mRNA is reverse transcribed by using oligo-dT, that has been hybridized to the polyadenylated tail of the mRNA, as a primer for a first cDNA strand. The second cDNA strand is synthesized using the enzymes DNA polymerase I, RNas H and *E. coli* DNA ligase. The double-stranded cDNA is fractioned to remove the shorter strands.

The resulting library was screened (Maniatis et al.) using an oligomer primer based on the amino acid sequence Asn Ala Cys Glu Met Trp Ala Thr Ala Ash Asp (SEQ ID No:2).

Isolated clones were found to encode TAI-1.

EXAMPLE 4

TAI-1 Expression

TAI-1 was expressed as a protein fusion in *E coli* using the expression vector pET3A (available from Novagen (Madison, Wis.) and described in Rosenberg et al., Gene 56 (1987) pp. 125-135).

cDNA encoding mature TAI-1 was obtained from an *O. moubata* lambda library according to the procedure of Example 3 and inserted into the vector downstream of a promoter recognized by the bacteriophage T7 RNA polymerase.

TAI-1 cDNA was inserted into the BamHI site of pET3A in frame with the first 11 amino acids of the T7 gene 10 protein. A Factor Xa cleavage site was inserted between gene 10 and TAI-1 to permit isolation of authentic TAI-1 containing no additional N-terminal residues. The resulting vector was named pET3A-TAI-1.

The vector was then inserted into *E. coli* BL21 (DE3) (available from Novagen (Madison, Wis.) described in Studier and Moffatt, *J. Mol. Biol.* 189 (1986) pp. 113-130), which contains the T7 RNA polymerase gene under control of the lac promoter.

IPTG was added to induce expression of polymerase, which acts exclusively on the T7 promoter, to generate high levels of TAI-1 transcript RNA which is translated in vivo, yielding TAI-1 protein.

A single *E. coli* BL21(DE3) transformant containing the pET3A-TAI-1 construct was used to inoculate an overnight culture (50 ml) of Luria Broth (Maniatis et al.) containing 50 mg/1 ampicillin. The culture was grown at 37° C. at 250 rpm for 16-20 hour. An inoculum of about 10 ml was added to 500 ml of fresh media in a 2 liter Erhlenmeyer flask and grown to an optical density of 0D600=0.4-0.8/ml. Isopropyl-beta-D-thiogalactopyranoside (IPTG) was then added to a final concentration of 1 mM to induce the lac operon. After about 3 hours of induction, the culture was harvested by centrifugation and the cells lysed by sonication.

Therapy

The proteinaceous substance of this invention, which inhibits adhesion of platelets to collagen, forms pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminium; and organic primary, secondary and tertiary amines, as for example, trialkylamines, including triethylamine, procaine, dibenzylamine, 1-ethenamine; N,N'-dibenzylethylenediamine, dihydroabietylamine, N-(lower)alkylpiperidine, and any other suitable amine.

The antithrombotic blood concentration of the proteinaceous substance of this invention which inhibits platelet adhesion to collagen is about 10 μg/ml.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Although the proteinaceous substance of this invention may survive passage through the gut following oral administration, applicants prefer non-oral administration, for example, subcutaneous, intravenous, intramuscular or intraperitoneal; administration by depot injection; or by implant preparation.

For parenteral administartion the proteinaceous substance of this invention may be administered as injectable dosages of a solution or suspension of the substamce in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The proteinaceous substance of this invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or sunthetic silicones, for example, Silastic, silicone rubber or other polymers manufactured by the Dow-Corning Corporation.

---

What is claimed is:

1. A substantially purified protein having the following amino acid composition:

| Amino acid | Residues/molecule |
|---|---|
| Asx | 12.3 |
| Thr | 10.4 |
| Ser | 17.3 |
| Glx | 19.8 |
| Gly | 15.9 |
| Ala | 8.6 |
| Cys | 4.0 |
| Val | 9.0 |
| Ile | 3.7 |
| Leu | 9.0 |
| Tyr | 3.7 |
| Phe | 4.0 |
| His | 1.9 |
| Lys | 6.9 |
| Arg | 7.9 |
| Pro | 8.9 |
| Trp | 2.0 |
| Met | 1.3 | having a molecular weight of about 15,600 which inhibits platelet adhesion to collagen and which does not inhibit platelet adhesion to fibrinogen or fibronectin, wherein residues/molecule is calculated based on amino acid composition analysis.

2. A therapeutic composition for inhibiting platelet adhesion to collagen comprising an effective amount of the protein of claim 1.

3. A method of treating a mammal for inhibiting platelet adhesion to collagen comprising administering to the mammal, in a therapeutically effective dose, the composition of claim 2.

* * * * *